(12) United States Patent
Kim et al.

(10) Patent No.: US 8,673,855 B2
(45) Date of Patent: Mar. 18, 2014

(54) PHOSPHATIDYLINOSITOL 3-KINASES ACTIVITY REGULATOR INCLUDING THE FIFTH ZINC FINGER DOMAIN OF FOG2

(75) Inventors: Vic Narry Kim, Seoul (KR); Jung Hyun Lee, Seoul (KR)

(73) Assignee: Seoul National University R&DB Foundation, Seoul (KR)

( * ) Notice: Subject to any disclaimer, the term of this patent is extended or adjusted under 35 U.S.C. 154(b) by 3 days.

(21) Appl. No.: 13/703,006

(22) PCT Filed: Jun. 8, 2010

(86) PCT No.: PCT/KR2010/003667
§ 371 (c)(1),
(2), (4) Date: Dec. 11, 2012

(87) PCT Pub. No.: WO2011/155643
PCT Pub. Date: Dec. 15, 2011

(65) Prior Publication Data
US 2013/0116185 A1    May 9, 2013

(51) Int. Cl.
*C07K 14/47*    (2006.01)

(52) U.S. Cl.
USPC ......... 514/16.4; 530/350; 530/326; 536/23.5; 435/320.1; 514/44 R; 514/19.3; 514/1.1

(58) Field of Classification Search
None
See application file for complete search history.

(56) References Cited

PUBLICATIONS

Huggins et al. J Biol Chem. 276(30);28029-28036:2001.*
Tevosian et al. Proc Natl Acad Sci USA. 96;950-955:1999.*
International Search Report for PCT/KR2010/003667.
Hyun, S. et al. Conserved microRNA miR-8/miR-200 and its target USH/FOG2 control growth by regulating PI3K, Cell, Dec. 11, 2009, vol. 139, pp. 1096-1108, See abstract, right colunm on p. 1103, figures 6, 7.
Svensson, E. C. et al. A functionally consrved N-terminal domain of the friend of GATA-2 (FOG-2) protein represses GATA4-dependent transcription, J. Bol. Chern., 2000, vol. 275, No. 27, pp. 20762-20769, See abstract and figure 6.
Taka Y A, T. et al. Identification of p300-targeted acetylated residues in GATA4 during hypertrophic responses in cardiac myocytes, J. Biol. Chern., 2008, vol. 283, No. 15, pp. 9828-9835, See abstract and figure 1.

* cited by examiner

*Primary Examiner* — Karlheinz R Skowronek
*Assistant Examiner* — Schuyler Milton
(74) *Attorney, Agent, or Firm* — The PL Law Group, PLLC

(57) ABSTRACT

The present invention relates to a phosphatidylinositol 3-kinases activity regulator which include the fifth zinc finger domain of FOG2 and which, more specifically, can induce cancer cells to die due to the inclusion of the fifth zinc finger domain of FOG2. Since the death of cancer cells is induced by suppressing the transfer of PI3K signals, the fifth zinc finger domain of FOG2 according to the present invention can be suitably use as a composition for the prevention and treatment of PI3K-related diseases.

2 Claims, 7 Drawing Sheets

A FOG2 domain structure

B Western blotting

C PI3K activity assay

D Western blotting

A Peptide sequence

| Name | Sequence | Length | Position |
|---|---|---|---|
| ZF-3-wt-21 | LKCTVCSYTADSVINFHQHLF | 21aa | 333-353aa |
| ZF-5-wt-24 | ATCFECNITFNNLDNYLVHKKHYC | 24aa | 547-570aa |
| ZF-5-m-24 | ATCFECNITFNNLDNYLVAKKAYC | 24aa | 547-570aa |
| ZF-5-wt-20 | CFECNITFNNLDNYLVHKKH | 20aa | 549-568aa |

B *in vitro* competition assay

C PI3K activity assay

D Western blotting

A Cell migration assay

B Cell migration assay

C Colony formation assay

A FACS analysis

HCT116

HCT116 pCK-flag | HCT116 FOG2-wt | HCT116 FOG2-ZF-5-m | HCT116 FOG2-ZF-6-m

B FACS analysis

Hep3B

Hep3B mock | Hep3B ZF-5-wt-24 | Hep3B ZF-3-m-24 | Hep3B ZF-5-wt-20

A MTT assay

B MTT assay

A FACS analysis

B FACS analysis

C FACS analysis

D FACS analysis

PHOSPHATIDYLINOSITOL 3-KINASES ACTIVITY REGULATOR INCLUDING THE FIFTH ZINC FINGER DOMAIN OF FOG2

CROSS REFERENCE TO RELATED APPLICATIONS AND CLAIM OF PRIORITY

This patent application claims benefit under 35 U.S.C. 119(e), 120, 121, or 365(c), and is a National Stage entry from International Application No. PCT/KR2010/003667, filed on Jun. 8, 2010, entire contents of which are incorporated herein by reference.

BACKGROUND

1. Field of the Invention

The present invention relates to a phosphatidylinositol 3-kinase activity regulator including the fifth zinc finger domain of FOG2.

2. Description of the Related Art

The Phosphatidylinositol 3-kinase (PI3K) which consists of p110 catalytic subunit and p85α regulatory subunit is a heterodimeric protein and activated by receptor tyrosine kinase (RTK) growth factors. The p85α regulatory subunit comprises multiple domains including two SH2 domains that are separated by inter-SH2(iSH2), which binds to p110 catalytic subunit. iSH2 domains that are required to bind to p110 consist of coiled-coil regions.

PI3K is a main downstream effector of receptor tyrosine kinases (RTK) and G protein-coupled receptors (GPCRs), mediates various intracellular signal transduction using phosphatidylinositol-3,4,5-triphosphates (PIP3), which is generated by phosphorylating PIP2. The downstream signal transduction of PI3K includes such as, RAC1, SGK, PKC, Akt, MDM2, FOXO1, NFκB, BAD, GSK3β and mTOR. The upstream signal transduction affected to PI3K activity includes PTEN, which is known to inhibit the RTK and PI3K activities regulated by insulin and growth factors.

Akt signal transduction is involved in the cell growth through NF-κB and Bcl2 consisting of the downstream signal transduction of Akt phosphorylated by PIP3. Akt signal transduction regulates the cell proliferation and death via controlling apoptosis by Fas (Trotman L C et al, Cancer Cell, 2003, 3:97-99) and also regulates cell cycles via p27 and glycogen synthase kinase 3 (GSK3) (Kiyokawa H et al, Cell, 1996, 85: 721-732; Hsieh F F et al, Blood, 2000, 96:2746-2754; Sears R et al., Genes Dev, 2000, 14: 2501-2514). Furthermore, Akt signal transduction increases the protein synthesis and the cell growth (cell size) by mTOR (mammalian target-of-rapamycin) and plays an important role in cell growth (Wullschleger S et al., Cell, 2006, 25:6423-6435).

As described above, PI3K is involved in various intracellular reactions and has been studied as a target of the disease which is caused by a abnormal signal transduction. Recently, it has been reported that the role of PI3K in autoimmune diseases including PI3K, systemic lupus erythematosus and rheumatoid arthritis; respiratory diseases including allergic asthma and chronic obstructive pulmonary disease; and cardiovascular disorders including atherosclerosis and myocardial infarction (Ghigo A et al., Bioessays, 2010, 32(3):185-96), and also reported the relation of intracellular insulin signal transduction and PI3K signal transduction (W. El Kholy et al., FASEB J. 2003, 17, 720-722).

In connection with cancers, PI3K regulates the cell growth and cell death and it has been targeted in cancer treatment researches via regulating the cancer cell proliferation, growth and cell death. PI3K performs an important role that regulates the cell motility in tumor metastasis. PI3K regulates cell motilities by enabling the cell migration and invasiveness and also regulates cell mobilities by controlling the actin dynamics through the interaction of p85α, small GTPase Rac and Cdc42. In addition, p85α subunit increases PI3K activity by interacting with intracellular proteins such as protein kinase C, SHP1, Rac, Rho, hormonal receptors, Ras and Src. Namely, increasing the cancer metastasis and cancer cell motility, PI3K activity is increased. Similarly, it has been reported the research of cancer treatments by using PI3K-pan inhibitors, specific PI3K isoform inhibitors or flavonoids (Hou D X, et al., Antiosid Redox Signal, 2010).

Additionally, in a metabolic disease, it has been demonstrated that p110 catalytic subunit of PI3K is an important role in metabolic regulation (Lazaros. C., et al, Nature letters, 2006). Accordingly, the abnormal signal transduction through the insulin receptor substrate (IRS) protein was shown in knock-out mice having the heterozygosity form (universally expressed) of p110 catalytic subunit. IRS is an important protein mediating the signal transduction of insulin-like growth factor 1 and leptin. Reacting with these hormones defectively, it was shown the somatic cell growth, hyperinsulinemia, glucose tolerance, hyperphagia and lipids increase.

In a cardiac disease, it has been reported that PI3K-PTEN signal transduction regulates the heart contractility and cardiac cell size (Michael A. et al., Cell, 2002). Accordingly, PI3K-PTEN signal transduction regulated various intracellular reactions and inactive PTEN, a tumor suppressor, reduced the heart contractility in myocardiocyteal muscle cells and caused a cardiomegaly. In other studies, it has been known that Class IA PI3K controlled the heart size and related with the cardiomegaly (Ji Luo et al, Molecular and Cellular Biology, 2005). The cardiomegaly was shown by overexpressing p110α of PI3K subunit, however, the heart was contracted by overexpressing the dominant negative p110α (Shioni, T., et al, EMBO, 2000).

Similarly the role of PI3K regulating the somatic cell proliferation, PI3K increased a stem cell proliferation in gain of function models which was increased PI(3,4,5)P3. Based on these results that PI3K inhibitor reduced the cell proliferation, it has been reported that PI3K facilitated the stem cell proliferation (Takahashi K et al., Biochem Soc. Trans. 2005, Vanhaesebroeck B. et al., Trends Biochem., 2005). However, it has been shown that the stem cell differentiation was promoted by PI3K inhibition and PI3K played an important role in retaining the pluripotency (Amstrong, L et al, Hum. Mol. Genet, 2006, Pyle, A. D. et al., Nat. Biotech., 2006, M. J Wellham et al., Biochem. Soc. Trans, 2007).

FOG2 (Friend of GATA 2) is one of transcriptional complement factors which is known to regulate GATA activity by binding to GATA transcription factors. FOG2 comprises eight zinc fingers including 4 C2H2-type and 4 C2H2-type zinc fingers. Recently, it has been reported that FOG2 can be regulated by miR-130 α in heart development. In our previous study, miR-200 family regulates a metabolic process such as the cell proliferation and survival by targeting FOG2 (S. Hyun., et al., Cell, 2009). Because these results are shown in a fly and human cells, it can be highly possible to conserve these processes evolutionarily. In mammal cell systems, FOG2, a negative regulator, directly bind to p85α and interferes with PI3K heterodimer complex (S. Hyun., et al., Cell, 2009).

Cys2His2 zinc-fingers (C2H2 zinc finger) of FOG2 protein mediate various bindings between protein-DNA or protein-protein. The zinc finger domain which has small size and self-folding protein structures, regulates interactions of zinc ions generally conserved in cysteine or histidine amino acids residues. These motifs forms ββα structures and are stabilized by combining zinc ions. However, there has been no report that FOG2 and its zinc finger domain have the anti-cancer activity.

Here, we investigate the PI3K activity which involves various intracellular mechanisms, and find out that the fifth zinc finger domain of FOG2 regulates PI3K/Akt activity, cancer cell migration and the reduction of cell survival.

SUMMARY

It is an object of this invention to provide an isolated polypeptide comprising the fifth zinc finger domain of FOG2 (Friend of GATA 2).

It is another object of this invention to provide an isolated nucleic acid sequence encoding the FOG2 polypeptide.

It is still another object of this invention to provide a vector comprising the nucleic acid sequence of encoding the FOG2 polypeptide.

It is further object of this invention to provide a host cell transfected by the vector.

It is further object of this invention to provide an anti-cancer agent or anti-cancer supplement agent, comprising as an active ingredient a component selected from the polypeptide, the nucleic acid and the vector.

It is further object of this invention to provide a composition for preventing or treating a metabolic disease, comprising as an active ingredient a component selected from the polypeptide, the nucleic acid and the vector.

It is further object of this invention to provide a composition for preventing or treating a cardiac disease, comprising as an active ingredient a component selected from the polypeptide, the nucleic acid and the vector.

It is further object of this invention to provide a composition for regulating a stem cell, comprising as an active ingredient a component selected from the polypeptide, the nucleic acid and the vector.

BRIEF DESCRIPTION OF THE DRAWINGS

FIG. 1A represents a structure of the zinc finger domain of FOG2;

FIG. 1B represents a result to analyze the interaction with p85α in the wild type and mutants of FOG2 according to Western blot analysis;

Figure 1:
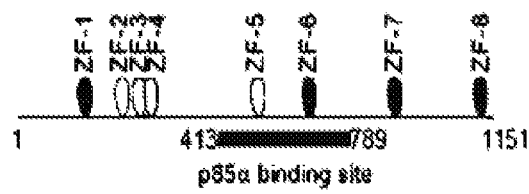
FIGS. 1A-1D represents a result to analyze inhibitory effects of the zinc finger domain of FOG2 on PI3K activity and Akt signaling.
Figure 1:
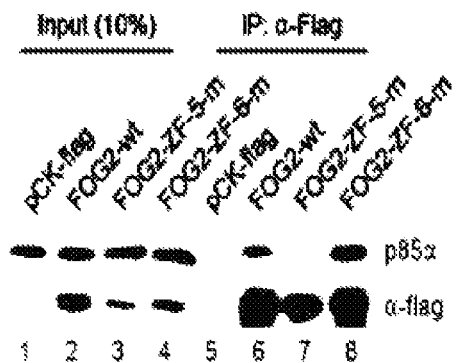
Figure 1:
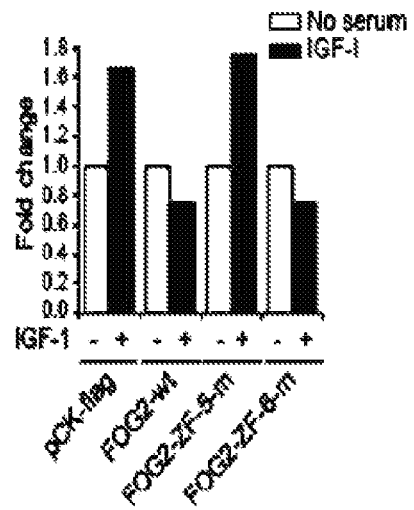
Figure 1:
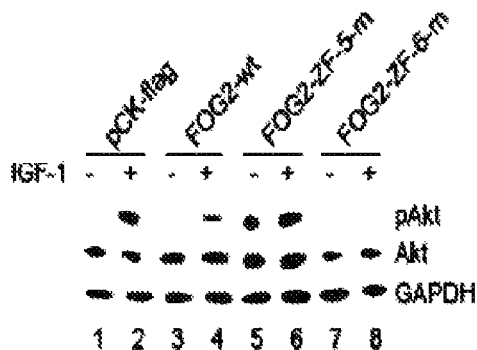
Figure 1:
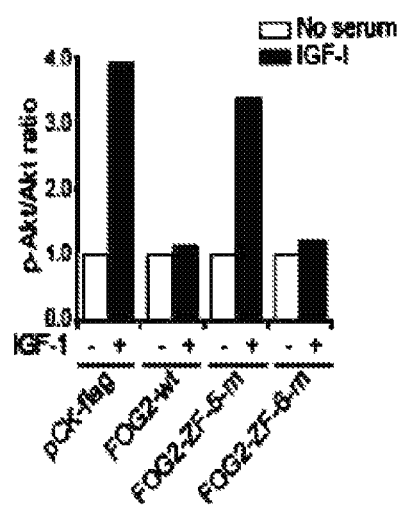

pCK-flag: Control;
FOG2-wt: The wild type of FOG2;
FOG2-ZF-5-m: Mutated FOG2 with altered the fifth zinc finger domain;
FOG2-ZF-6-m: Mutated FOG2 with altered the sixth zinc finger domain;

FIG. 1C is a graph showing PI3K activity changes by the zinc finger domain of FOG2;

pCK-flag: Control;
FOG2-wt: The wild type of FOG2;
FOG2-ZF-5-m: Mutated FOG2 with altered the fifth zinc finger domain;
FOG2-ZF-6-m: Mutated FOG2 with altered the sixth zinc finger domain.

FIG. 1D is a graph showing Akt level changes by the zinc finger domain of FOG2;

pCK-flag: Control;
FOG2-wt: The wild type of FOG2;
FOG2-ZF-5-m: Mutated FOG2 with altered the fifth zinc finger domain; and
FOG2-ZF-6-m: Mutated FOG2 with altered the sixth zinc finger domain.

FIGS. 2A-2C represents a result to analyze inhibitory effects of zinc finger domain peptides of FOG2 on PI3K activity;

FIG. 2A represents sequences, lengths and position of the zinc finger domain peptides of FOG2;

FIG. 2B is a graph showing the results of a in vitro competition assay;

ZF-3-wt-21: The peptide not comprising the fifth zinc finger domain of FOG2;
ZF-5-wt-24: The peptide comprising a portion of the fifth zinc finger domain of FOG2;

FIG. 2C is a graph showing PI3K activity changes by synthesized zinc finger domain peptides of FOG2;

Mock: Dimethylsulfoxide (DMSO);
ZF-5-wt-24: The peptide comprising a portion of the fifth zinc finger domain of FOG2 (24 amino acids);
ZF-5-m-24: The peptide comprising a portion of the fifth zinc finger domain of FOG2 (24 amino acids);
ZF-5-wt-20: The peptide comprising a portion of the fifth zinc finger domain of FOG2 (20 amino acids);
ZF-3-wt-21: The peptide not comprising the fifth zinc finger domain of FOG2;

FIG. 2D is a graph showing Akt activity changes by the synthesized zinc finger domain peptides of FOG2;

Mock: DMSO; and
ZF-5-wt-24: The peptide comprising a portion of the fifth zinc finger domain of FOG2 (24 amino acids).

FIGS. 3A-3C represents a result to analyze the cancer cell migration and colony formation by zinc finger domain of FOG2 and synthesized zinc finger domain peptides of FOG2:

FIG. 3A is a graph showing the cancer cell migration by zinc finger domain of FOG2;

pCK-flag: Control;
FOG2-wt: The wild type of FOG2;
FOG2-ZF-5-m: Mutated FOG2 with altered the fifth zinc finger domain;
FOG2-ZF-6-m: Mutated FOG2 with altered the sixth zinc finger domain;

FIG. 3B is a graph showing the cancer cell migration by synthesized zinc finger domain peptides of FOG2;

Mock: DMSO;
ZF-5-wt-24: The peptide comprising a portion of the fifth zinc finger domain of FOG2 (24 amino acids);
ZF-5-m-24: The peptide comprising a portion of the fifth zinc finger domain of FOG2 (24 amino acids);
ZF-5-wt-20: The peptide comprising a portion of the fifth zinc finger domain of FOG2 (20 amino acids);
ZF-3-wt-21: The peptide not comprising the fifth zinc finger domain of FOG2; and FIG. 3C represents a result to analyze a cancer cell colony formation by synthesized zinc finger domain peptides of FOG2.

FIGS. 4A-4B represents a result to analyze the cell death induced by zinc finger domain of FOG2:

FIG. 4A is a graph showing the cell death induced by zinc finger domain of FOG2 in HCT116 cells according to FACS analysis;

pCK-flag: Control;
FOG2-wt: The wild type of FOG2;
FOG2-ZF-5-m: Mutated FOG2 with altered the fifth zinc finger domain;
FOG2-ZF-6-m: Mutated FOG2 with altered the sixth zinc finger domain;

FIG. 4B is a graph showing the cell death induced by synthesized zinc finger domain peptides of FOG2 in Hep3B cells according to FACS analysis;
   Mock: DMSO;
   ZF-5-wt-24: The peptide comprising a portion of the fifth zinc finger domain of FOG2 (24 amino acids);
   ZF-5-m-24: The peptide comprising a portion of the fifth zinc finger domain of FOG2 (24 amino acids); and
   ZF-5-wt-20: The peptide comprising a portion of the fifth zinc finger domain of FOG2 (20 amino acids).
FIGS. 5A-5B represents a result to analyze an PI3K inhibition effect of zinc finger domain of FOG2:
FIG. 5A is a graph showing the PI3K inhibition by zinc finger domain of FOG2 in Hep3B cells;
   pCK-flag: Control;
   FOG2-wt: The wild type of FOG2;
   FOG2-ZF-5-m: Mutated FOG2 with altered the fifth zinc finger domain;
   FOG2-ZF-6-m: Mutated FOG2 with altered the sixth zinc finger domain;
FIG. 5B is a graph showing the PI3K inhibition by synthesized zinc finger domain peptides of FOG2 in MDA MB 231 cells;
   Mock: DMSO;
   ZF-5-wt-24: The peptide comprising a portion of the fifth zinc finger domain of FOG2 (24 amino acids);
   ZF-5-m-24: The peptide comprising a portion of the fifth zinc finger domain of FOG2 (24 amino acids);
   ZF-5-wt-20: The peptide comprising a portion of the fifth zinc finger domain of FOG2 (20 amino acids); and
   ZF-3-wt-21: The peptide not comprising the fifth zinc finger domain of FOG2.
FIGS. 6A-6B represents a result to analyze the cell proliferation effect by zinc finger domain of FOG2 and synthesized zinc finger domain peptides:
FIG. 6A is a graph showing the cell proliferation effect by zinc finger domain of FOG2 in MDA MB 231 cells according to MTT assay;
   pCK-flag: Control;
   FOG2-wt: The wild type of FOG2;
   FOG2-ZF-5-m: Mutated FOG2 with altered the fifth zinc finger domain;
   FOG2-ZF-6-m: Mutated FOG2 with altered the sixth zinc finger domain;
FIG. 6B is a graph showing the cell proliferation effect by synthesized zinc finger domain peptides of FOG2 in MDA MB 231 cells;
   ZF-5-wt-24: The peptide comprising a portion of the fifth zinc finger domain of FOG2 (24 amino acids); and
   ZF-5-m-24: The peptide comprising a portion of the fifth zinc finger domain of FOG2 (24 amino acids).
FIGS. 7A-7D represents a result to analyze PI3K inhibition by FOG2 fragments, zinc finger domain of FOG2 and synthesized zinc finger domain peptides of FOG2:
FIG. 7A is a graph showing an apoptotic effect by FOG2 fragments in MDA MB 231 cells according to FACS analysis;
   pCK-flag: Control;
   FOG2[1-1151]: The full-length FOG2 protein;
   FOG2[1-412]: The FOG2 protein comprising the amino acid sequence ranging 1-412th amino acid residues of FOG2 full-length amino acid sequence;
   FOG2[413-789]: The FOG2 protein comprising the amino acid sequence ranging 413-789$^{th}$ amino acid residues of FOG2 full-length amino acid sequence;
   FOG2[802-1151]: The FOG2 protein comprising the amino acid sequence ranging 802-1151$^{th}$ amino acid residues of FOG2 full-length amino acid sequence;

FIG. 7B is a graph showing the apoptotic effect by the zinc finger domain of FOG2 in MDA MB 231 cells according to FACS analysis;
   pCK-flag: Control;
   FOG2-wt: The wild type of FOG2;
   FOG2-ZF-5-m: Mutated FOG2 with altered the fifth zinc finger domain;
   FOG2-ZF-6-m: Mutated FOG2 with altered the sixth zinc finger domain;
FIG. 7C is a graph showing the apoptotic effect by synthesized zinc finger domain peptides of FOG2 in MDA MB 231 cells according to FACS analysis;
   Mock: DMSO;
   ZF-5-wt-24: The peptide comprising a portion of the fifth zinc finger domain of FOG2 (24 amino acids);
   ZF-5-m-24: The peptide comprising a portion of the fifth zinc finger domain of FOG2 (24 amino acids);
   ZF-5-wt-20: The peptide comprising a portion of the fifth zinc finger domain of FOG2 (20 amino acids);
FIG. 7D is a graph showing the apoptotic effect by synthesized zinc finger domain peptides of FOG2 in MCF7 cells according to FACS analysis;
   Mock: DMSO;
   ZF-5-wt-24: The peptide comprising a portion of the fifth zinc finger domain of FOG2 (24 amino acids);
   ZF-5-m-24: The peptide comprising a portion of the fifth zinc finger domain of FOG2 (24 amino acids);
   ZF-5-wt-20: The peptide comprising a portion of the fifth zinc finger domain of FOG2 (20 amino acids); and
   ZF-3-wt-21: The peptide not comprising the fifth zinc finger domain of FOG2.

DETAILED DESCRIPTION

The present disclosure will be described in further detail hereinbelow.

In one aspect of this invention, there is provided an isolated polypeptide comprising the fifth zinc finger domain of FOG2 (Friend of GATA 2).

The present inventors have made intensive studies to regulate PI3K activity which involved multiple cellular mechanisms. As a result, the present inventors have found out that the fifth zinc finger domain of FOG2 regulates PI3K and Akt activities and reduces the cancer cell migration and survival.

The polypeptide of the present invention consists of 20-500 amino acids, but is not limited thereto.

The polypeptide comprises the amino acid sequence ranging 548-571th amino acid residues of FOG2 full-length amino acid sequence as set forth in SEQ ID NO:1, but is not limited thereto.

The polypeptide comprises the amino acid sequence ranging 413-789$^{th}$ amino acid residues of FOG2 full-length amino acid sequence as set forth in SEQ ID NO:1, but is not limited thereto.

The cancer to be treated by the present polypeptide is selected from the group consisting of chronic lymphocytic leukemia, breast cancer, cervical cancer, fibrosarcoma, myosarcoma, liposarcoma, chondrosarcoma, osteogenic sarcoma, chordomas, angiomyosarcoma, endotheioblastoma, lymphangiosarcoma, lymphangioendotheioblastoma, synovioma, mesothelioma, Ewing tumor, leiomyosarcoma, rhabdomyosarcoma, stomach cancer, esophageal cancer, colon cancer, colon cancer, pancreatic cancer, ovarian cancer, prostate cancer, uterine cancer, head and neck cancer, skin cancer, brain cancer, squamous cell cancer, sebaceous gland tumor, papillary neoplasm, nipple adenoma, cystadenocarcinoma, medulla tumor, bronchogenic tumor, kidney cancer, liver cancer, gallbladder cancer, cholangiocarcinoma, choriocarcinoma, seminoma, embryoma, Wilm's tumor, testis cancer, lung cancer, small cell lung cancer, non-small cell lung cancer, bladder cancer, epithelioma, glioma, astrocytoma, medulloblastoma, craniopharyngioma, ependymoma, pinealoma, hemangioblastoma, aucoustic neuroma, oligodendrogliomas, meningioma, malignant melanoma, neuroblastoma, retinoblastoma, leukemia, lymphoma and Kaposi's sarcoma, but not limited to.

In another aspect of this invention, there is provided an isolated nucleic acid sequence encoding the FOG2 polypeptide.

The nucleic acid comprises amino acid sequences as set forth in SEQ ID NO:1, but not limited to.

In another aspect of this invention, there is provided a vector comprising the isolated nucleic acid encoding the FOG2 polypeptide.

The expression vector of the present invention is a vector in which FOG2 gene is inserted. The expression vector refers to plasmids, viruses or other mediators that are typically used in the art, but not limited to.

In another aspect of this invention, there is provided a host cell transfected by the vector.

The expression vector of the present invention is transfected to the cells according to various methods known in the art. For example, transient transfection, microinjection, transduction, cell fusion, calcium phosphate precipitation, liposome-mediated transfection, DEAE Dextran-mediated transfection, polybrene-mediated transfection, electroporation, gene gun and methods used in the art may be used for delivering the nucleic acid into the host cell (Wu et al, J. Bio. Chem., 267:963-967, 1992; Wu and Wu, J. Bio. Chem., 263: 14621-14624, 1988).

In another aspect of this invention, there is provided an anti-cancer agent, comprising as an active ingredient a component selected from the polypeptide, the nucleic acid and vector.

According to an embodiment of the present invention, the zinc finger domain of FOG2 interacts with the p85α as a subunit of PI3K and PI3K activity is inhibited by overexpressing FOG2-ZF-wt. Furthermore, Akt and PI3K which are activated by IGF-1 are inhibited by overexpressing FOG2-ZF-wt (FIG. 1).

Figure 5:
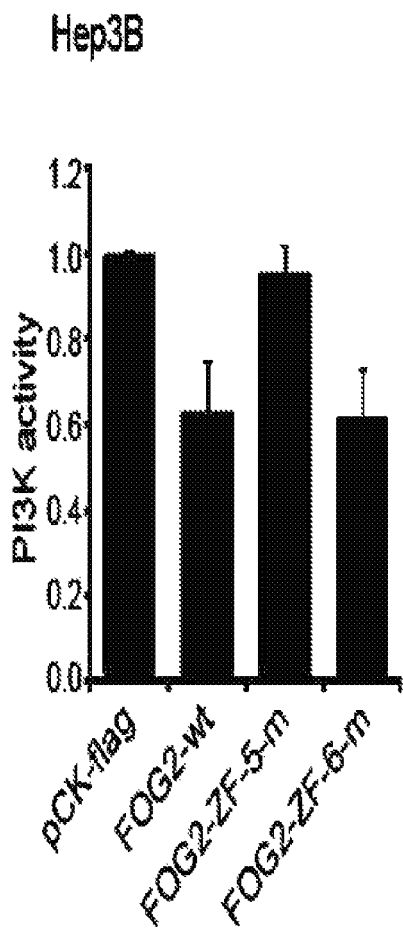
Figure 5:
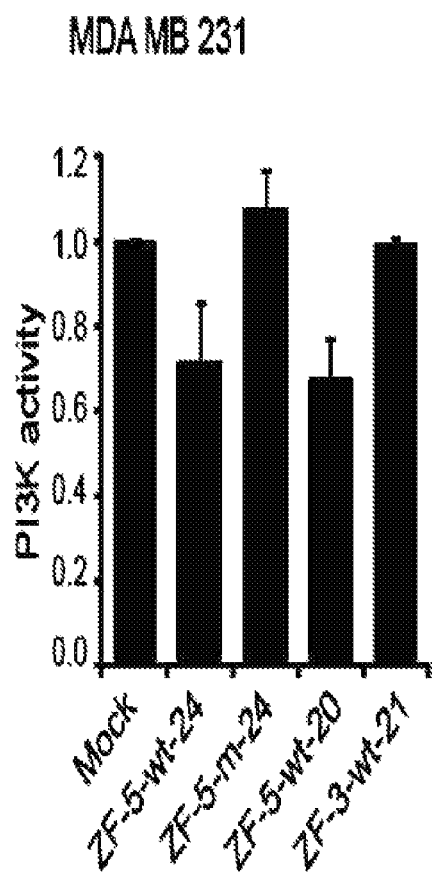

According to an embodiment of the present invention, the inhibitory effect of PI3K activity is reduced by overexpressing FOG2-ZF-5-m in various cancer cells, which has the similar activity to the control. These results indicate that wild type polypeptides of FOG2 (ZF-5-wt-24, ZF-5-wt-20) decrease PI3K activity while FOG2 mutant with altered zinc finger domain (ZF-5-m-24) does not affect to PI3K activity (FIG. 5).

Figure 2:
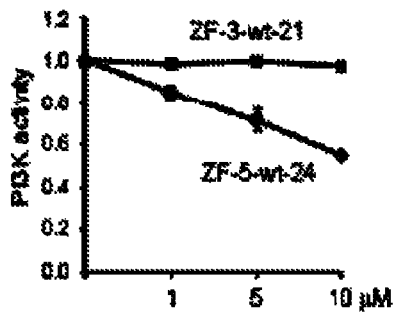
Figure 2:
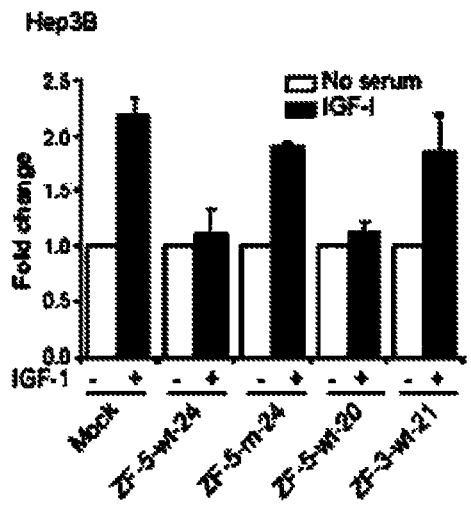
Figure 2:
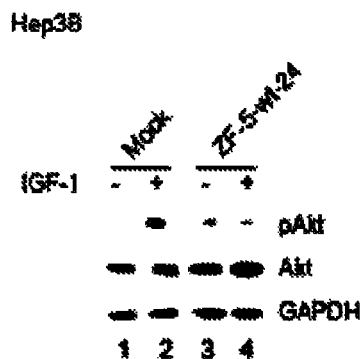
Figure 2:
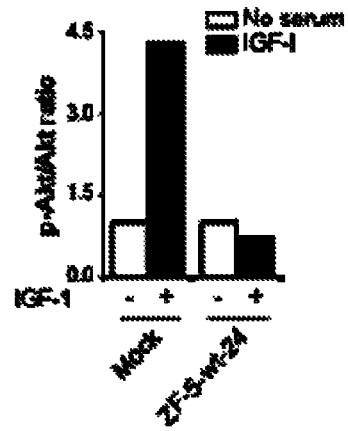

According to an embodiment of the present invention, to reveal whether the above effect is caused by zinc finger domains of FOG2, FOG2 mutants (20-24 amino acids) having modified amino acid residues of the zinc finger domain are synthesized, and treated cancer cells. PI3K activity is inhibited and Akt activation induced by IGF-1 is also inhibited by treating the fifth zinc finger domain peptides (FIG. 2).

Figure 6:
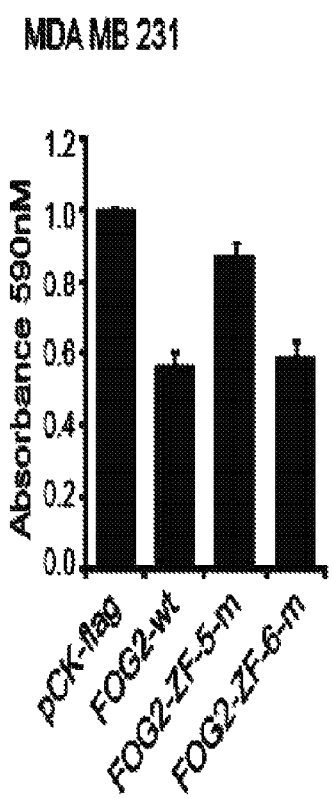
Figure 6:
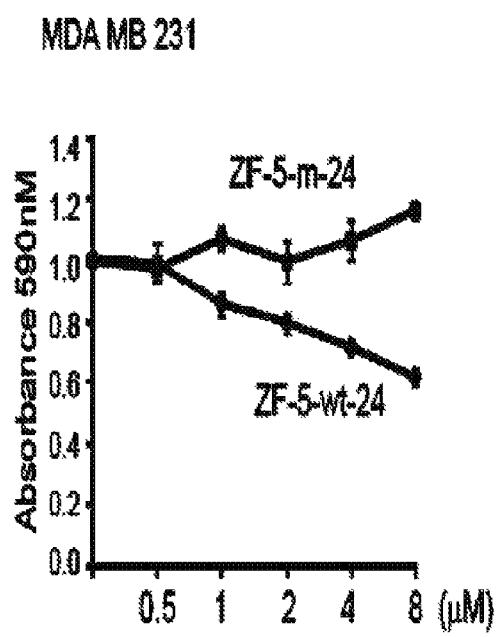

According to an embodiment of the present invention, the wild type polypeptide of FOG2 (ZF-5-wt-24) reduces the cancer cell proliferation, while FOG2 mutant (ZF-5-m-24) having modified the fifth zinc finger domains does not (FIG. 6).

Figure 3:
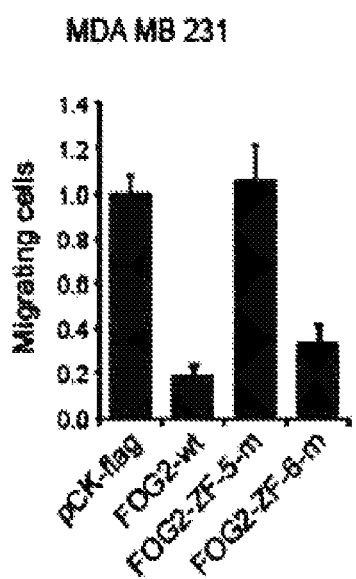
Figure 3:
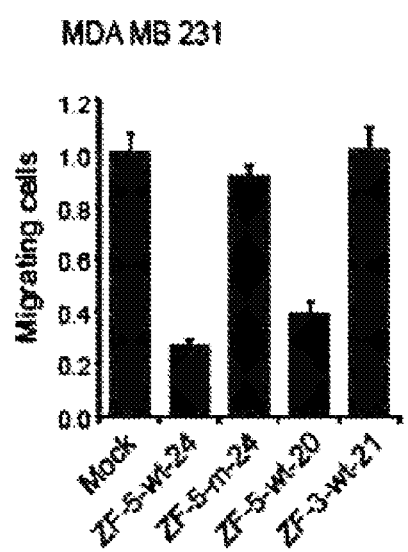
Figure 3:
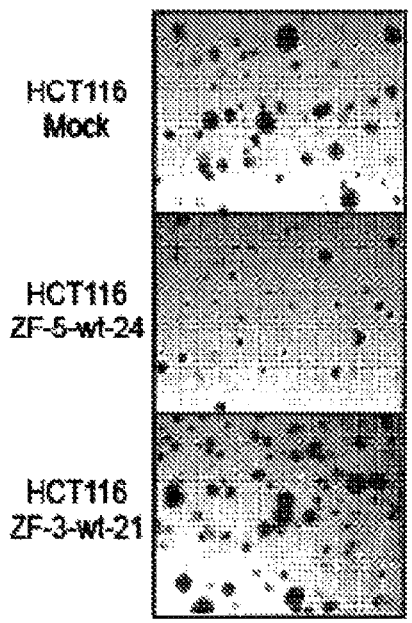
Figure 3:
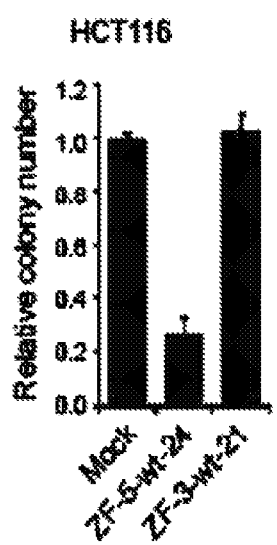

According to an embodiment of the present invention, the overexpression of FOG2 for testing the anti-cancer effect of the FOG2 zinc finger domain reduces the cell migration, while the overexpression of FOG2 mutant (FOG2-ZF-5-m) does not. These results demonstrate that the synthesized zinc finger domain peptide of FOG2 (ZF-5-wt-24) and the mutant (ZF-5-m-24) have the similar effect on reducing the cell migration inhibition, therefore, the FOG2 zinc finger domain has anti-cancer effects. In addition, cancer cells were treated with synthesized zinc finger domain peptides of FOG2 and subject to the colony formation assay. The FOG2 wild type (ZF-5-wt-24) reduces the colony formation while FOG2 mutant have no difference with the control shown by the colony formation pictures. After treating peptides, the generated colonies were counted and shown in graphs. ZF-5-wt-24 reduces the number of colony by one fifth, ZF-5-m-21 was similar to the control (FIG. 3).

Figure 4:
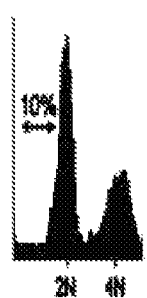
Figure 4:
Figure 4:
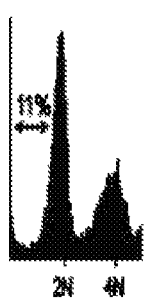
Figure 4:
Figure 4:
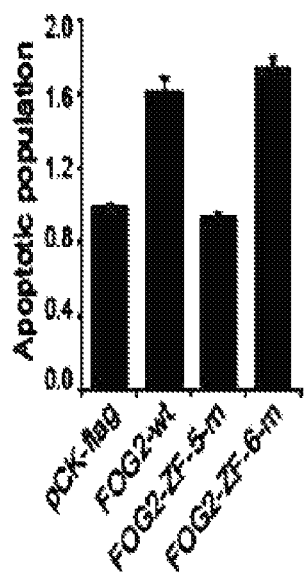
Figure 4:
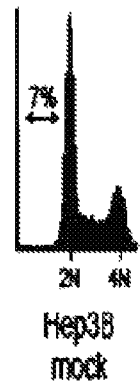
Figure 4:
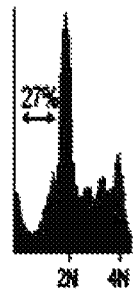
Figure 4:
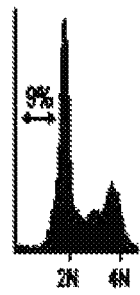
Figure 4:
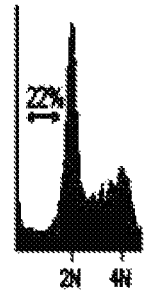
Figure 4:
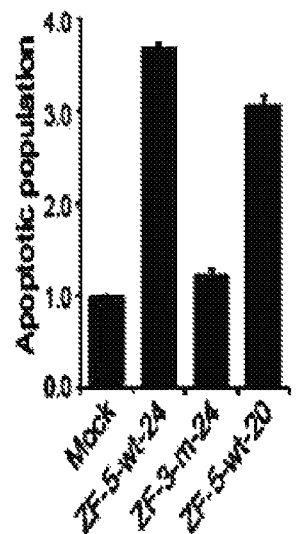

According to an embodiment of the present invention, to test whether the apoptotic effect of the FOG2 zinc finger domain reduces the cell migration, the FOG2 wild type (FOG2-wt) and the mutant (FOG2-ZF-5-m and FOG2-ZF-6-m) were overexpressed in cancer cells. In FACS analysis, the FOG2-ZF-5-m overexpression reduces apoptosis. This result indicates that the fifth zinc finger domain of FOG2 has the anti-cancer effect. ZF-5-wt-24 reduces the cell apoptosis (FIG. 4).

Figure 7:
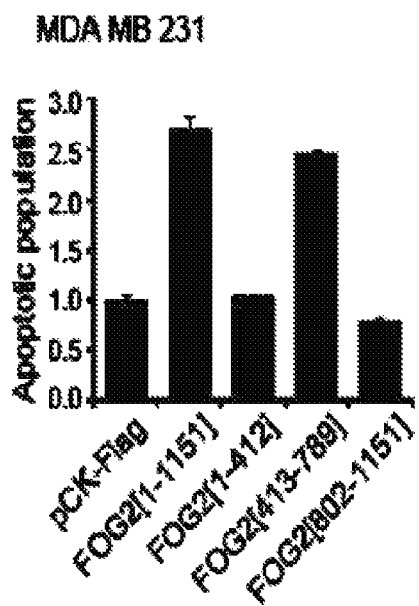
Figure 7:
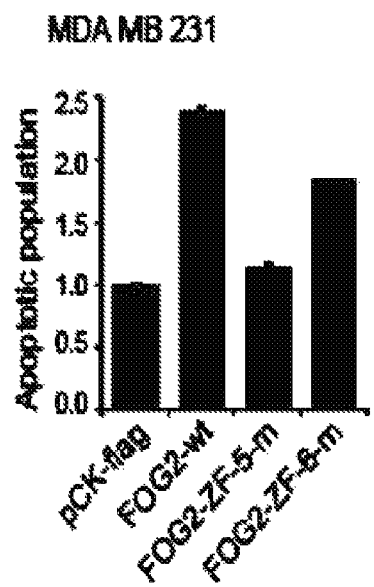
Figure 7:
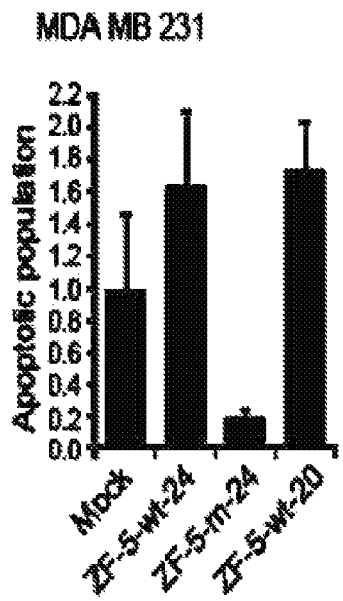
Figure 7:
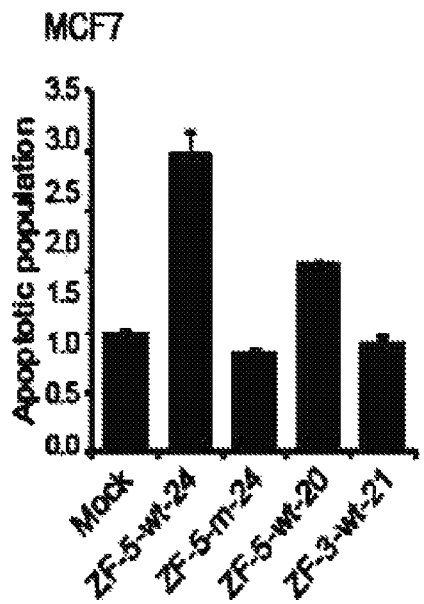

To investigate the anti-cancer effect of the fifth zinc finger domain of the full-length FOG2[1-1151], FOG2 fragments [1-412], [413-789] and [802-1151] were prepared and overexpressed in cells. The full-length FOG2[1-1151] and FOG2 [1-412] fragment comprising the fifth zinc finger domain reduces the apoptosis when they are overexpressed. This result is confirmed by analyzing the apoptotic effect of FOG2-ZF-5m overexpression. This anti-cancer effect of the fifth zinc finger domain of FOG2 is tested by analyzing the apoptotic effect of FOG2-ZF-5m. Furthermore, the synthesized fifth zinc finger domain peptides were treated two types of cancer cells and then shown the anti-cancer effect of the zinc finger domain (FIG. 7).

Therefore, the fifth zinc finger domain of FOG2 may be used in a anti-cancer agent as it is shown that inhibits PI3K/Akt activities, the cancer cell migration and the colony formation.

A pharmaceutically effective amount of an anti-cancer agent, comprising the fifth zinc finger domain of FOG2 for preventing and treating a cancer will be varied according to the administration method, target region and condition of the patient. The amount of the compositions administering to a subject will be determined the adequate mount with considering the safety and efficiency. An effective amount in humans can be estimated from that of animal determined by a animal testing. For example, the consideration for determining the effective amount disclosed in Hardman and Limbird, eds., Goodman and Gilman's The Pharmacological Basis of Therapeutics, 10$^{th}$ ed. (2001), Pergamon Press; and E.W. Martin ed., Remington's Pharmaceutical Sciences, 18th ed. (1990), Mack Publishing Co.

The composition according to the present invention may further include a carrier, diluents, an excipient or the combination thereof. The pharmaceutically acceptable carrier is not limited if it delivers the fifth zinc finger domain of FOG2 into the body. For example, compounds disclosed in Merck Index, 13th ed., Merck & Co. Inc., a saline solution, a sterilized water, Ringer's solution, a buffered saline solution, dextrose solution, maltodextrin solution, glycerol, ethanol and the combination thereof were used for the carrier. In addition, the composition of the present invention may further include an additive agent, such as an antioxidant, a buffer or a bacteristat as necessary. The composition according to the present invention may further include a diluents, a dispersing agent, a surfactant, a binder and a lubricant. The formulations include a solution, a suspension, an emulsion, a globule, a capsule, a granule or a tablet. Details of suitable formulations according to a disease and an ingredient can be found in Remington's Pharmaceutical Sciences (Mack Publishing Company, Easton Pa., 18th, 1990).

A composition of this invention may be administered orally or parenterally (e.g. intravenous injection, subcutaneous injection, intraperitoneal injection and a part application). The dosage of the compositions of this invention will be varied according to the age, body weight and sex of the patient, condition of the patient, diet, time of administration, the mode of application, the excretion rate and severity of the disease. The composition of the present invention may be administered at a daily dosage of 0.001 µg-10 mg/kg (body weight), more preferably 0.01 µg-10 mg/kg. The composition may be preferably administered to a subject once a day or several times a day as divided portions.

The composition according to the present invention may further include one or more additional ingredients which have the same or similar functions. The composition of the present invention generally comprises 0.0001-10 wt % (preferably 0.001-1 wt %) of the polypeptide.

In another aspect of this invention, there is provided an anti-cancer supplement agent, comprising as an active ingredient a component selected from the polypeptide, the nucleic acid and the vector.

According to an embodiment of the present invention, the overexpression of the FOG2 zinc finger domain inhibits PI3K/Akt activities, the cancer cell migration, and the colony formation. Accordingly, the fifth zinc finger domain of FOG2 may be used in an anti-cancer supplement agent.

A pharmaceutically effective amount of an anti-cancer supplement agent, comprising the fifth zinc finger domain of FOG2 for preventing and treating a cancer will be varied according to the administration method, target region and condition of the patient. The amount of the compositions administering to a subject will be determined the adequate mount with considering the safety and efficiency. An effective amount in humans can be estimated from that of animal determined by a animal testing. For example, the consideration for determining the effective amount disclosed in Hardman and Limbird, eds., Goodman and Gilman's The Pharmacological Basis of Therapeutics, 10th ed. (2001), Pergamon Press; and E. W. Martin ed., Remington's Pharmaceutical Sciences, 18th ed. (1990), Mack Publishing Co.

The composition according to the present invention may further include a carrier, a diluents, an excipient or the combination thereof. The pharmaceutically acceptable carrier is not limited if it delivers the fifth zinc finger domain of FOG2 into the body. For example, compounds disclosed in Merck Index, 13$^{th}$ ed., Merck & Co. Inc., a saline solution, a sterilized water, Ringer's solution, a buffered saline solution, dextrose solution, maltodextrin solution, glycerol, ethanol and the combination thereof were used for the carrier. In addition, the composition of the present invention may further include an additive agent, such as an antioxidant, a buffer or a bacteristat as necessary. The composition according to the present invention may further include a diluents, a dispersing agent, a surfactant, a binder and a lubricant. The formulations include a solution, a suspension, an emulsion, a globule, a capsule, a granule or a tablet. Details of suitable formulations according to a disease and an ingredient can be found in Remington's Pharmaceutical Sciences (Mack Publishing Company, Easton Pa., 18th, 1990).

A composition of this invention may be administered orally or parenterally (e.g. intravenous injection, subcutaneous injection, intraperitoneal injection and a part application). The dosage of the compositions of this invention will be varied according to the age, body weight and sex of the patient, condition of the patient, diet, time of administration, the mode of application, the excretion rate and severity of the disease. The composition of the present invention may be administered with a daily dosage of 0.001 µg-10 mg/kg (body weight), more preferably 0.01 µg-10 mg/kg. The composition may be preferably administered to a subject once a day or several times a day as divided portions.

The composition according to the present invention may further include one or more additional ingredients which have the same or similar functions. The composition of the present invention generally comprises 0.0001-10 wt % (preferably 0.001-1 wt %) of the polypeptide.

In another aspect of this invention, there is provided a method for treating a cancer, comprising administering to a subject with the cancer a composition comprising a pharmaceutically effective amount of an ingredient selected from the FOG2 polypeptide, the nucleic acid and the vector.

In another aspect of this invention, there is provided a method for preventing a cancer, comprising administering to a subject with the cancer a composition comprising a pharmaceutically effective amount of an ingredient selected from the FOG2 polypeptide, the nucleic acid and the vector.

In another aspect of this invention, there is provided a use of an ingredient selected from the FOG2 polypeptide, the nucleic acid and the vector, for manufacturing a composition for the treatment of a cancer.

The subjects include mammals, such as humans, non-human primates, mice, rats, dogs, cats, rabbits, horses and cows, but not limited to.

In another aspect of this invention, there is provided a composition for preventing or treating a metabolic disease, comprising as an active ingredient a component selected from the FOG2 polypeptide, the nucleic acid and the vector.

In another aspect of this invention, there is provided a method for treating a metabolic disease, comprising administering to a subject with the metabolic disease a composition comprising a pharmaceutically effective amount of an ingredient selected from the FOG2 polypeptide, the nucleic acid and the vector.

In another aspect of this invention, there is provided a use of an ingredient selected from the FOG2 polypeptide, the nucleic acid and the vector, for manufacturing a composition for the treatment of a metabolic disease.

According to an embodiment of the present invention, the overexpression of the FOG2 zinc finger domain inhibits PI3K/Akt activities and consequently improves a PI3K-related metabolic disease (Lazaros C. et al, Nature Letters, 2006).

The metabolic disease is selected from the group consisting of hyperinsulinaemia, glucose tolerance, hyperphagia, obesity, diabetes mellitus, insulin resistance, disorders of lipid metabolism, hypertriglyceridemia and hypertension, but is not limited thereto. The subjects include mammals, such as humans, non-human primates, mice, rats, dogs, cats, rabbits, horses and cows, but not limited to.

In another aspect of this invention, there is provided a composition for preventing or treating a cardiac disease, comprising as an active ingredient a component selected from the polypeptide, the nucleic acid and the vector.

In another aspect of this invention, there is provided a method for treating a cardiac disease, comprising administering to a subject with the cardiac disease a composition comprising a pharmaceutically effective amount of an ingredient selected from the FOG2 polypeptide, the nucleic acid and the vector.

In another aspect of this invention, there is provided a method for preventing a cardiac disease, comprising administering to a subject with the cardiac disease a composition comprising a pharmaceutically effective amount of an ingredient selected from the FOG2 polypeptide, the nucleic acid and the vector.

In another aspect of this invention, there is provided a use of an ingredient selected from the FOG2 polypeptide, the nucleic acid and the vector, for manufacturing a composition for the treatment of a cardiac disease.

According to an embodiment of the present invention, the overexpression of the FOG2 zinc finger domain inhibits PI3K/Akt activities and consequently improves a PI3K-related cardiac disease (Michael A., et al, Cell, 2002, Ji Luo, et al, Molecular and Cellular Biology, 2005).

The cardiac disease is selected from the group consisting of ischaemic heart disease, heart failure, fibrillation or flutter of heart and arrhythmia, but is not limited thereto. The subjects include mammals, such as humans, non-human primates, mice, rats, dogs, cats, rabbits, horses and cows, but not limited to.

In another aspect of this invention, there is provided a composition for regulating a stem cell, comprising as an active ingredient a component selected from the polypeptide, the nucleic acid and the vector.

In another aspect of this invention, there is provided a method for regulating a stem cell proliferation and differentiation, comprising treating to the stem cell a composition comprising an ingredient a component selected from the polypeptide, the nucleic acid and the vector.

In another aspect of this invention, there is provided a use of an ingredient selected from the polypeptide, the nucleic acid and the vector for manufacturing a composition for regulating a stem cell proliferation and differentiation.

According to an embodiment of the present invention, the overexpression of the FOG2 zinc finger domain inhibits PI3K/Akt activities and consequently suppresses a PI3K-related stem cell differentiation (Michael A., et al, Cell, 2002, Ji Luo, et al, Molecular and Cellular Biology, 2005).

EXAMPLES OF THE INVENTION

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Cell Culture

Hep3B cell (Korean Cell Line Bank), HCT116 cell (Korean Cell Line Bank) and 293T cell (American Type Culture Collection) were cultured with Dulbecco's modified Eagle medium (DMEM) supplemented with 10% fetal bovine serum. The cell lines were maintained at 37° C. in a humidified incubator with 5% $CO_2$. The cells ($5 \times 10^5$ cells/plate) were cultured in 100 mm dishes. After incubation for 3 days, the experiments were performed as below:

Example 2

Preparation of Expression Vectors for the Zinc Finger Domain of FOG2

To obtain the FOG2-wt (the wild type), the full-length FOG2 cDNA was digested with BamHI and NotI enzymes, after which the fragment was cloned into the pCK-flag vector.

In addition, to investigate whether FOG2 interacts with p85α, FOG2 mutants having altered zinc finger domain (FOG-ZF-5-m and FOG-ZF-6-m) was prepared by mutating two domains (known to interact with p85α) positioned from 413 to 789$^{th}$ amino acid residues of FOG2. In the fifth and sixth zinc finger domains, two histidine residues of amino acid residues interacting with zinc were substituted with alanine residues using the QuickChange Site-Directed Mutagenesis kit.

The primers for the QuickChange Site-Directed Mutagenesis are shown as follows:

```
The fifth zinc finger domain:
Forward primer (SEG ID NO: 2):
5'-AATTATCTAGTGCGCAAAAAGCGTTATTGCAGCAGCCGA-3';

a. Reverse primer (SEG ID NO: 3):
5'-TCGGCTGCTGCAATAACGCTTTTTGCGCACTAGATAATT-3';

a. The sixth zinc finger domain:
b. Forward primer (SEG ID NO: 4):
5'-GAAACATACATGGTCCGCAAACAGTATTACCGTGCTACACGCCACG
AC-3';
and a. Reverse primer (SEG ID NO: 5):
5'-GTCGTGGCGTGTAGCACGGTAATACTGTTTGCGGACCATGTATGTT
TC-3';
```

Example 3

Synthesis of Zinc Finger Domain Peptides of FOG2

We synthesized the amino acids sequence ranging 548-571th amino acid residues of the FOG2 full-length amino acid sequence as set forth in SEQ ID NO:1 and several mutated sequences. The amino acid sequences were synthesized and purified in Peptron Inc. (Purity 80%) (Table 1).

TABLE 1

| Name | Sequence | Number of amino acid | Position |
|---|---|---|---|
| ZF-3-wt-21 | LKCTV CSYTA DSVIN FHQHL F (SEQ ID NO:16) | 21 | 335-355 |
| ZF-5-wt-24 | ATCFE CNITF NNLDN YLVHK KHYC (SEQ ID NO:17) | 24 | 548-571 |
| ZF-5-m-24 | ATCFE CNITF NNLDN YLVAK KAYC | 24 | 548-571 |
| ZF-5-wt-20 | CFECN ITFNN LDNYL VHKKH | 20 | 550-569 |

Example 4

Synthesis of FOG2 Fragments

Each polynucleotide for the truncated FOG2 mutants was amplified using the following primers and the FOG2 full-length cDNA as a template: 95° C., 5 min; [95° C., 30 s; 55° C., 30 s; and 72° C., 1 min] for 30 cycles.

```
FOG2[1-412];
Forward primer (SEQ ID NO: 6):
5'-GGATCCATGTCCCGGCGAAAGCAAAGC-3';

Reverse primer (SEQ ID NO: 7):
5'-GCGGCCGCGTGGCTGGCTGTAAGCTGTC-3';

FOG2[413-789];
Forward primer (SEQ ID NO: 8):
5'-GGATCCCAGACTTATTGACCAGAAG-3';

Reverse primer (SEQ ID NO: 9):
5'-GCGGCCGCGATATCACATCTTGGGTGGTAG-3'

FOG2[802-1151];
Forward primer (SEQ ID NO: 10):
5'-GGATCCCTCTGACGATCAACAAGTG-3';

Reverse primer (SEQ ID NO: 11):
5'-GCGGCCGCTCATTTGACATGTTCTGCTGCATG-3';

FOG2[1-506];
Forward primer (SEQ ID NO: 12):
5'-GGATCCATGTCCCGGCGAAAGCAAAGC-3';

Reverse primer (SEQ ID NO: 13):
5'-GCGGCCGCTCATTTGACATGTTCTGCTGCATG-3';

FOG2[1-789];
Forward primer (SEQ ID NO: 14):
5'-GGATCCATGTCCCGGCGAAAGCAAAGC-3';
and Reverse primer (SEQ ID NO: 15):
5'-GCGGCCGCTCATTTGACATGTTCTGCTGCATG-3'.
```

The PCR products were digested with BamHI and NotI restriction enzymes and inserted into pCK-flag vector digested with the same restriction enzymes.

Experimental Example 1

Interaction Between the FOG2 Zinc Finger Domain and the p85α Regulatory Component <1-1> Investigation for Interaction of the FOG2 Zinc Finger Domain and the p85α Regulatory Component To reveal the region of FOG2 interacting with p85α as a subunit of PI3K, we numbered eight (8) zinc finger domains of FOG2. Then, mutated FOG2 with altered zinc finger domain (FOG-ZF-5-m and FOG-ZF-6-m) was manufactured by mutating two domains (known to interact with p85α) positioned at 413-789$^{th}$ amino acid residues of FOG2.

Hep3B cells were transfected with pCK-flag (control), FOG2-wt (wild type) and FOG2 mutants having modified the zinc finger domain (FOG2-ZF-5-m and FOG2-ZF-6-m). On 2 days after transfection, the lysates were obtained using the lysis buffer (20 mM Hepes (pH7.4), 100 mM NaCl, 20 mM KAc, 10 mM MgCl$_2$, 10 M ZnCl$_2$, 1 mM Na$_3$VO$_4$, 5 mM NaF, 1% NPO$_4$). The cell lysates were immunoprecipitated with the α-Flag (Sigma, A2220) and subject to the Western blot analysis using p85α (sc-1637, Santa Cruz) and α-Flag antibody (Sigma, F1804).

As shown in FIG. 1, it is analyzed that FOG2-ZF-6-m interacts with p85α while FOG2-ZF-5-m did not (FIG. 1B).

<1-2> Inhibitory Effect of the FOG2 Zinc Finger Domain on PI3K Activity

To investigate the inhibitory effect to PI3K activity by FOG2 zinc finger domain, PI3K activity was analyzed using FOG2 mutants having modified zinc finger domain. Specially, it is known that IGF signaling pathway plays an important role in cancer and the increased IGF-1 level enhances the risk of various cancers in many researches.

Accordingly, the PI3K activity was increased by incubating Hep3B cells with IGF-1 and then measured when the cells were incubated with peptides having mutated FOG2 zinc finger domain.

After Hep3B cells incubation, 100 ng/ml IGF-1 (Insulin like growth factor-1) was added to the cells and incubated for 30 min.

Hep3B cells were transfected with pCK-flag (control), FOG2-wt (wild type) and FOG2 mutants having modified zinc finger domain (FOG2-ZF-5-m and FOG2-ZF-6-m). Two days later, the lysates were obtained using a lysis buffer (20 mM Hepes (pH7.4), 100 mM NaCl, 20 mM KAc, 10 mM MgCl$_2$, 10 mM ZnCl$_2$, 1 mM Na$_3$VO$_4$, 1% NPO$_4$). The cell lysates were immunoprecipitated with p85α(sc-1637, Santa Cruz) and Protein G-Sepharose beads using the same method above. After binding to beads, the lysates were washed 2 times with the lysis buffer and one time with the wash buffer (0.1 M Tris-HCl (pH 7.4), 5 mM LiCl, and 0.1 mM Na$_3$VO$_4$).

For measurement of PI3K activity, 10 μl of sonicated PIP$_2$ (1 μg/μl, Calbiochem), 10 μl of 100 mM MgCl$_2$ and 1 μl of [−$^{32}$P]ATP (500 μCi/ml) were added to the kinase buffer (10 mM Tris-HCl (pH 7.4), 150 mM NaCl, 1 mM Na$_3$VO$_4$, 10 mM ZnCl$_2$) and incubated at 37° C. for 30 min. After incubation, 20 μl of 6 N HCl was added to stop the reaction and PIP$_2$ was extracted by treatment with 200 μl of methanol: chloroform (1:1) solution. The amount of radioactively labeled PIP$_2$ in the extract was measured using a scintillator counter.

As represented in FIG. 5, the PI3K activity in cells transfected with FOG2-wt was not altered without IGF-1 stimulation; however, the FOG2-ZF-5m mutant having modified fifth zinc finger domain did not inhibit PI3K activity. Furthermore, as shown in FIG. 1C, FOG2-ZF-5m did not inhibit PI3K activation by IGF-1 stimulation (FIG. 1C and FIG. 5), similar to results under IGF-1 non-stimulation conditions.

<1-3> Inhibitory Effect of FOG2 Zinc Finger Domain on Akt Activity

IGF-1 is the most potent activator in Akt signaling pathway. Hep3B cells were transfected with FOG2 mutants having modified zinc finger domain to measure the effect on the Akt signaling by FOG2-ZF-5m. The Akt activity was measured by analyzed Akt phosphorylation.

Hep3B cells were transfected with pCK-flag (control), FOG2-wt (wild type) and FOG2 mutants having modified zinc finger domain (FOG2-ZF-5-m and FOG2-ZF-6-m) and stimulated with IGF-1. The expression of Akt (Cell signaling Technology, USA), pAkt (Cell signaling Technology, USA) and GAPDH(Santa cruz, USA) were measured by Western blot analysis.

As shown in FIG. 1D, the Akt phosphorylation was decreased when FOG2-wt and FOG2-ZF-6-m was transfected after the IGF-1 stimulation. However, the Akt phosphorylation was increased in FOG2-ZF-5-m, demonstrating that FOG2-ZF-5-m is not capable of inhibiting the PI3K activation by IGF-1 stimulation (FIG. 1D).

Experimental Example 2

Inhibitory Effect on PI3k Activity and Akt Signaling by Zinc Finger Domain Peptide of FOG2

<2-1> Inhibitory Effect of Zinc Finger Domain Peptides of FOG2 on PI3K Activity

To investigate whether the zinc finger domain per se interacts with p85α, MDA MB 231 cells were incubated with four types of zinc finger domain peptides for 48 hr, and the PI3K activity was analyzed. For peptide treatment, cells were trypsinized to detach them from a culture dish and their aliquot ($2 \times 10^5$ cells) was incubated with 4 μM peptides in 100 mm dishes. The control was incubated with Mock (DMSO).

As shown in FIG. 5B, ZF-5-m-24 inhibited the PI3K activity by approximately 30% relative to ZF-5-wt-24 in MDA MB 231 breast cancer cells (FIG. 5B).

In addition, Hep3B liver cancer cells were incubated with 4 μM peptides for 48 hr and the PI3K activity was analyzed. As shown in FIG. 2C, ZF-5-wt-24 and ZF-5-wt-20 inhibited the IGF-1-induced PI3K activation; however, ZF-5-m-24 and ZF-3-wt-21 did not inhibit (FIG. 2C).

<2-2> In Vitro Competition Analysis

The in vitro competition analysis was performed by PI3K immunoprecipitation in 293T cells. The activated PI3K was extracted from the 293T cell lysates by immunoprecipitating with p85α antibody simultaneously with addition of the synthesized peptides (1 μM, 5 μM and 10 μM). The PI3K activation was induced as described above.

As a result, as shown in FIG. 2B, ZF-5-wt-24 reduced the PI3K activity by about 40% in a dose-dependent manner as compared with the positive control ZF-3-wt-21 (FIG. 2B).

<2-3> Inhibitory Effect on the Cell Proliferation by Zinc Finger Domain Peptide of FOG2

Because the PI3K activation is critical in cell growth, the cell proliferation was analyzed to investigate the inhibitory effect of the FOG2 zinc finger domain using the MTT assay.

MDA MB 231 cells were seeded in a 96-well plate, and transfected with 100 ng DNA of pCKflag, FOG2-wt, FOG2-ZF-5-m or FOG2-ZF-6-m using Lipofectamine 2000. On 3 days post-transfection, the MTT assay was performed. MDA MB 231 cells ($2 \times 10^3$ cells) were seeded in a 96-well plate and treated with 4 μM each peptide for 3 days. After the treatment, 50 μl of MTT solution (2 mg/ml) was added to each well, incubated at 37° C. for 1 hr. Then, 150 μl of DMSO was added to each well and the absorbance value of each well was measured at 590 nm using a microplate reader.

As shown in FIG. 6A, FOG2-wt, FOG2-ZF-6-m and ZF-5-wt-24 were shown to reduce the cell proliferation by about 40%. However, FOG2-ZF-5-m did not influence the cell proliferation (FIG. 6A). In addition, as shown in FIG. 6B, when the synthesized peptide was treated with MDA MB 231 cells, the inhibitory effect of ZF-5-wt-24 on the cell proliferation became more prominent as ZF-5-wt-24 concentration increased (FIG. 6B).

<2-4> Inhibitory Effect of Zinc Finger Domain Peptides of FOG2 on Akt Signaling

To test whether the Akt activity induced by IGF-1 treatment is inhibited by the synthesized peptides, Hep3B cells were incubated with IGF-1 and ZF-5-wt-24 for 24 hr and the expressions of Akt and pAkt were analyzed.

Hep3B cells were incubated with 4 μM ZF-5-wt-24 for 2 days and then further incubated in a serum-free media for 24 hr. Afterwards, the cells were incubated with IGF-1 for 30 min and subject to the Western blot analysis. Mock (DMSO) was used as a control.

As a result, as shown in FIG. 2D, the Akt phosphorylation induced by IGF-1 stimulation was reduced by the treatment of ZF-5-wt-24 (FIG. 2D), demonstrating that the fifth domain peptide of FOG2 plays a critical role in PI3K activity inhibition.

Experimental Example 3

Anti-Cancer Effect of FOG2 Zinc Finger Domain

<3-1> Cell Migration Inhibition of FOG2 Zinc Finger Domain

PI3K activation has been reported to cause cancer aggravation by inducing the cell migration. We tested whether the FOG2 overexpression promotes the cell migration.

MDA MB 231 cells were transfected with pCK-flag (control), FOG2-wt (wild type) and FOG2 mutants having modified zinc finger domain (FOG2-ZF-5-m and FOG2-ZF-6-m). The cell migration was then analyzed using the modified Boyden chamber method (Albini A et al., Cancer Res 1987 47:3239-45). Following the transfection for 24 hr, MDA MB 231 cells ($1 \times 10^5$) were suspended in a serum-free medium and seeded in triplicate in the upper part of BD chamber (8 mm pore size). The lower part was filled with the serum-free medium. Following the incubation at 37° C. for 18 hr, non-migrating cells positioned at the upper surface of filters were cleaned with a cotton swab. The migrating cells passing through the lower surface of filters were fixed with 70% ethanol and treated with the Giemsa staining solution for 50 min. Then, the cells were rinsed with water and observed under a microscope. The cell migration rate was determined by counting the number of cells present in randomly-selected six sections and the migration range was expressed as the average number of cells per a microscopic field.

As shown in FIG. 3A, FOG2-wt and FOG2-ZF-6-m were shown to reduce the cell migration by approximately 80%. However, such reduction of the cell migration was not observed for the FOG2-ZF-5-m, which is similar to the control pCK-flag (FIG. 3A).

<3-2> Cell Migration Inhibition by Synthesized Peptides of FOG2 Zinc Finger Domain PI3K activation has been reported to cause cancer aggravation by inducing the cell migration. We investigated whether synthesized peptides decrease the cell migration.

MDA MB 231 cells were incubated with 4 μM Mock (control, DMSO), 4 μM ZF-5-wt-24, 4 μM ZF-5-m-24, 4 μM ZF-5-wt-20 or 4 μM ZF-3-wt-21. After treatment, the cell migration was analyzed using the modified Boyden chamber method (Albini A et al., Cancer Res 1987 47:3239-45). After 2 days of treatment, MDA MB 231 cells ($1 \times 10^5$) were suspended in the serum free medium and seeded in triplicate in the upper part of BD chamber (8 mm pore size). The lower part was filled with the serum free medium. Following the incubation at 37° C. for 18 hr, non-migrating cells positioned at the upper surface of filters were cleaned with the cotton swab. The migrating cells passing through the lower side surface of filters were fixed with 70% ethanol and stained using the Giemsa stain method. The cell migration rate was determined by counting the number of cells present in randomly-selected six sections and the migration range was expressed as the average number of cells per a microscopic field.

As shown in FIG. 3B, ZF-5-wt-24 and ZF-5-wt-20 were shown to reduce the cell migration. However, such reduction of the cell migration was not observed for ZF-5-m-24 and ZF-5-wt-21 (FIG. 3B).

<3-3> Colony Formation Inhibition of Synthesized Peptides of FOG2 Zinc Finger Domain PI3K activation has been reported to cause the cancer aggravation by inducing the colony formation. We tested whether the FOG2 overexpression inhibits the colony formation.

HCT116 cells ($1\times10^3$) were trypsinized and seeded in triplicate in a six-well plate. The serum-free medium containing the synthesized peptide in <Example 3> and 0.3% agar was incubated with the cells. One week after treatment, the generated colony was visualized with 0.5 mg/ml NBT (Nitro blue tetrazolium chloride) and the colonies over 1 mm in diameter were counted.

As shown in FIG. 3C, the number of colonies was reduced when HCT116 cells were treated with ZF-5-wt-24 (FIG. 3C). These results demonstrated that FOG2 zinc finger domain may serve as a negative regulator to the cancer cell migration and the colony formation.

Experimental Example 4

Apoptosis Induction by FOG2 Fragment and Zinc Finger Domain

<4-1> Apoptosis Induction by the FOG2 Fragment

PI3K inactivation has been reported to cause cancer cell apoptosis, and FOG2 is known to inhibit the PI3K activity. To test whether PI3K inactivation by overexpressing FOG2 induces apoptosis, MDA MB 231 cells overexpressed FOG2 were analyzed with FACS.

MDA MB 231 cells were incubated with Full-FOG2[1-1151], FOG2[1-412], FOG2[413-789] or FOG2[802-1151]. The cells ($5\times10^4$) were seeded in a 12-well plate and transfected with 1 μg of Full-FOG2[1-1151], FOG2[1-412], FOG2[413-789] or FOG2[802-1151] using Lipofectamine 2000. The cells were incubated at 37° C. for 2 days and subject to FACS analysis.

The cells were incubated with FOG2 fragments and fixed with 70% ethanol for 16 hr. The fixed cells were stained using RNase (5 mg/ml) and propidium iodide (50 mg/ml). The amount of DNA in stained cells was analyzed with Cell Quest program of FACS caliber (Becton Dickinson).

As shown in FIG. 7A, the number of apoptotic cells was increased upon treatment with Full-FOG2[1-1151] or FOG2 [413-789] (FIG. 7A).

<4-2> Apoptosis Induction of the FOG2 Zinc Finger Domain in HCT116 Cells

PI3K inactivation is known to cause cancer cell apoptosis, and FOG2 is known to inhibit PI3K activity. To test whether PI3K inactivation by overexpressing FOG2 induces apoptosis, HCT116 cells transfected with pCK-flag (control), FOG2-wt (wild type) and FOG2 mutants (FOG2-ZF-5-m and FOG2-ZF-6-m) were analyzed with FACS.

As shown in FIG. 4A, FOG2-wt (wild type) and FOG2-ZF-6-m increased apoptosis 2 days after transfection except for FOG2-ZF-5-m (FIG. 4A). These results were consistent with FIG. 7B that apoptosis were induced in MDA MB 231 cells transfected with pCK-flag (control), FOG2-wt (wild type) and FOG2 mutants (FOG2-ZF-5-m and FOG2-ZF-6-m) (FIG. 7B).

<4-3> Apoptosis Induction of the FOG2 Zinc Finger Domain in Hep3B Cells

PI3K inactivation is known to cause cancer cell apoptosis, and FOG2 is known to inhibit PI3K activity. To test whether PI3K inactivation by overexpressing FOG2 induces apoptosis, Hep3B cells treated with the peptide synthesized in <Experiment 3> were analyzed with FACS.

As a result, as shown in FIG. 4B, ZF-5-wt-24 and ZF-5-wt-20 induced apoptosis after 48 hr of treatment (FIG. 4B). Moreover, ZF-5-wt-24 and ZF-5-wt-20 also promoted apoptosis in other cancer cell line, MDA MB 231 and MCF 7 (FIG. 7C and FIG. 7D).

The fifth zinc finger domain of FOG2 is responsible for inhibition of PI3K activity and Akt signaling as well as induction of cancer cell apoptosis. In particular, it has been discovered that mutations in the fifth zinc finger domain of FOG2 result in decrease in the inhibitory effects on PI3K and Akt signaling and decrease in cancer cell apoptosis, urging us to reason that the fifth zinc finger domain of FOG2 is effectively used in compositions for preventing and treating PI3K-related diseases.

As disclosed above, the fifth zinc finger domain of FOG2 can be used in developing for manufacturing a composition for the treatment of a cancer, a metabolic disease, and a cardiac disease, and a stem cell regulation.

---

What is claimed is:

1. A method for treating cancer, diabetes or obesity, the method comprising administering to a subject in need thereof a composition comprising an ingredient effective to regulate cell proliferation and differentiation, the ingredient selected from the group consisting of:
   a polypeptide consisting of the amino acid sequence of SEQ ID NO: 17 or SEQ ID NO: 19;
   a synthetic nucleic acid sequence encoding a polypeptide consisting of the amino acid sequence of SEQ ID NO: 17 or SEQ ID NO: 19; and
   a vector comprising the nucleic acid encoding the polypeptide of SEQ ID NO: 17 or SEQ ID NO: 19.

2. The method of claim 1, wherein the cancer is selected from the group consisting of chronic lymphocytic leukemia, breast cancer, cervical cancer, fibrosarcoma, myosarcoma, liposarcoma, chondrosarcoma, osteogenic sarcoma, chordomas, angiomyosarcoma, endothelioblastoma, lymphangiosarcoma, lymphangioendothelioblastoma, synovioma, mesothelioma, Ewing tumor, leiomyosarcoma, rhabdomyosarcoma, stomach cancer, esophageal cancer, colon cancer, colon cancer, pancreatic cancer, ovarian cancer, prostate cancer, uterine cancer, head and neck cancer, skin cancer, brain cancer, squamous cell cancer, sebaceous gland tumor, papillary neoplasm, nipple adenoma, cystadenocarcinoma, medulla tumor, bronchogenic tumor, kidney cancer, liver cancer, gallbladder cancer, cholangiocarcinoma, choriocarcinoma, seminoma, embryoma, Wilm's tumor, testis cancer, lung cancer, small cell lung cancer, non-small cell lung cancer, bladder cancer, epithelioma, glioma, astrocytoma, medulloblastoma, craniopharyngioma, ependymoma, pinealoma, hemangioblastoma, aucoustic neuroma, oligodendrogliomas, meningioma, malignant melanoma, neuroblastoma, retinoblastoma, leukemia, lymphoma and Kaposi's sarcoma.

* * * * *

SEQUENCE LISTING

```
<160> NUMBER OF SEQ ID NOS: 19

<210> SEQ ID NO 1
<211> LENGTH: 1151
<212> TYPE: PRT
<213> ORGANISM: Homo sapiens

<400> SEQUENCE: 1

Met Ser Arg Arg Lys Gln Ser Lys Pro Arg Gln Ile Lys Arg Pro Leu
1               5                   10                  15

Glu Asp Ala Ile Glu Asp Glu Glu Glu Cys Pro Ser Glu Glu Thr
            20                  25                  30

Asp Ile Ile Ser Lys Gly Asp Phe Pro Leu Glu Glu Ser Phe Ser Thr
        35                  40                  45

Glu Phe Gly Pro Glu Asn Leu Ser Cys Glu Glu Val Glu Tyr Phe Cys
    50                  55                  60

Asn Lys Gly Asp Asp Glu Gly Ile Gln Glu Thr Ala Glu Ser Asp Gly
65                  70                  75                  80
```

```
Asp Thr Gln Ser Glu Lys Pro Gly Pro Gly Val Glu Thr Asp Asp
                 85                  90                  95
Trp Asp Gly Pro Gly Glu Leu Glu Val Phe Gln Lys Asp Gly Glu Arg
                100                 105                 110
Lys Ile Gln Ser Arg Gln Leu Pro Val Gly Thr Thr Trp Gly Pro
                115                 120                 125
Phe Pro Gly Lys Met Asp Leu Asn Asn Asn Ser Leu Lys Thr Lys Ala
    130                 135                 140
Gln Val Pro Met Val Leu Thr Ala Gly Pro Lys Trp Leu Leu Asp Val
145                 150                 155                 160
Thr Trp Gln Gly Val Glu Asp Asn Lys Asn Asn Cys Ile Val Tyr Ser
                165                 170                 175
Lys Gly Gly Gln Leu Trp Cys Thr Thr Thr Lys Ala Ile Ser Glu Gly
                180                 185                 190
Glu Glu Leu Ile Ala Phe Val Val Asp Phe Asp Ser Arg Leu Gln Ala
                195                 200                 205
Ala Ser Gln Met Thr Leu Thr Glu Gly Met Tyr Pro Ala Arg Leu Leu
210                 215                 220
Asp Ser Ile Gln Leu Leu Pro Gln Gln Ala Met Ala Ser Ile Leu
225                 230                 235                 240
Pro Thr Ala Ile Val Asn Lys Asp Ile Phe Pro Cys Lys Ser Cys Gly
                245                 250                 255
Ile Trp Tyr Arg Ser Glu Arg Asn Leu Gln Ala His Leu Met Tyr Tyr
                260                 265                 270
Cys Ser Gly Arg Gln Arg Glu Ala Ala Pro Val Ser Glu Glu Asn Glu
                275                 280                 285
Asp Ser Ala His Gln Ile Ser Ser Leu Cys Pro Phe Pro Gln Cys Thr
    290                 295                 300
Lys Ser Phe Ser Asn Ala Arg Ala Leu Glu Met His Leu Asn Ser His
305                 310                 315                 320
Ser Gly Val Lys Met Glu Glu Phe Leu Pro Pro Gly Ala Ser Leu Lys
                325                 330                 335
Cys Thr Val Cys Ser Tyr Thr Ala Asp Ser Val Ile Asn Phe His Gln
                340                 345                 350
His Leu Phe Ser His Leu Thr Gln Ala Ala Phe Arg Cys Asn His Cys
    355                 360                 365
His Phe Gly Phe Gln Thr Gln Arg Glu Leu Leu Gln His Gln Glu Leu
    370                 375                 380
His Val Pro Ser Gly Lys Leu Pro Arg Glu Ser Asp Met Glu His Ser
385                 390                 395                 400
Pro Ser Ala Thr Glu Asp Ser Leu Gln Pro Ala Thr Asp Leu Leu Thr
                405                 410                 415
Arg Ser Glu Leu Pro Gln Ser Gln Lys Ala Met Gln Thr Lys Asp Ala
                420                 425                 430
Ser Ser Asp Thr Glu Leu Asp Lys Cys Glu Lys Lys Thr Gln Leu Phe
    435                 440                 445
Leu Thr Asn Gln Arg Pro Glu Ile Gln Pro Thr Thr Asn Lys Gln Ser
    450                 455                 460
Phe Ser Tyr Thr Lys Ile Lys Ser Glu Pro Ser Ser Pro Arg Leu Ala
465                 470                 475                 480
Ser Ser Pro Val Gln Pro Asn Ile Gly Pro Ser Phe Pro Val Gly Pro
                485                 490                 495
Phe Leu Ser Gln Phe Ser Phe Pro Gln Asp Ile Thr Met Val Pro Gln
```

```
                500             505             510
    Ala Ser Glu Ile Leu Ala Lys Met Ser Glu Leu Val His Arg Arg Leu
                515                 520                 525
    Arg His Gly Ser Ser Ser Tyr Pro Val Ile Tyr Ser Pro Leu Met
        530                 535                 540
    Pro Lys Gly Ala Thr Cys Phe Glu Cys Asn Ile Thr Phe Asn Asn Leu
    545                 550                 555                 560
    Asp Asn Tyr Leu Val His Lys Lys His Tyr Cys Ser Ser Arg Trp Gln
                    565                 570                 575
    Gln Met Ala Lys Ser Pro Glu Phe Pro Ser Val Ser Glu Lys Met Pro
                580                 585                 590
    Glu Ala Leu Ser Pro Asn Thr Gly Gln Thr Ser Ile Asn Leu Leu Asn
                595                 600                 605
    Pro Ala Ala His Ser Ala Asp Pro Glu Asn Pro Leu Leu Gln Thr Ser
            610                 615                 620
    Cys Ile Asn Ser Ser Thr Val Leu Asp Leu Ile Gly Pro Asn Gly Lys
    625                 630                 635                 640
    Gly His Asp Lys Asp Phe Ser Thr Gln Thr Lys Lys Leu Ser Thr Ser
                        645                 650                 655
    Ser Asn Asn Asp Asp Lys Ile Asn Gly Lys Pro Val Asp Val Lys Asn
                    660                 665                 670
    Pro Ser Val Pro Leu Val Asp Gly Glu Ser Asp Pro Asn Lys Thr Thr
                675                 680                 685
    Cys Glu Ala Cys Asn Ile Thr Phe Ser Arg His Glu Thr Tyr Met Val
            690                 695                 700
    His Lys Gln Tyr Tyr Cys Ala Thr Arg His Asp Pro Pro Leu Lys Arg
    705                 710                 715                 720
    Ser Ala Ser Asn Lys Val Pro Ala Met Gln Arg Thr Met Arg Thr Arg
                    725                 730                 735
    Lys Arg Arg Lys Met Tyr Glu Met Cys Leu Pro Glu Gln Glu Gln Arg
                    740                 745                 750
    Pro Pro Leu Val Gln Gln Arg Phe Leu Asp Val Ala Asn Leu Asn Asn
                755                 760                 765
    Pro Cys Thr Ser Thr Gln Glu Pro Thr Glu Gly Leu Gly Glu Cys Tyr
    770                 775                 780
    His Pro Arg Cys Asp Ile Phe Pro Gly Ile Val Ser Lys His Leu Glu
    785                 790                 795                 800
    Thr Ser Leu Thr Ile Asn Lys Cys Val Pro Val Ser Lys Cys Asp Thr
                    805                 810                 815
    Thr His Ser Ser Val Ser Cys Leu Glu Met Asp Val Pro Ile Asp Leu
                820                 825                 830
    Ser Lys Lys Cys Leu Ser Gln Ser Glu Arg Thr Thr Thr Ser Pro Lys
            835                 840                 845
    Arg Leu Leu Asp Tyr His Glu Cys Thr Val Cys Lys Ile Ser Phe Asn
            850                 855                 860
    Lys Val Glu Asn Tyr Leu Ala His Lys Gln Asn Phe Cys Pro Val Thr
    865                 870                 875                 880
    Ala His Gln Arg Asn Asp Leu Gly Gln Leu Asp Gly Lys Val Phe Pro
                    885                 890                 895
    Asn Pro Glu Ser Glu Arg Asn Ser Pro Asp Val Ser Tyr Glu Arg Ser
                900                 905                 910
    Ile Ile Lys Cys Glu Lys Asn Gly Asn Leu Lys Gln Pro Ser Pro Asn
            915                 920                 925
```

-continued

```
Gly Asn Leu Phe Ser Ser His Leu Ala Thr Leu Gln Gly Leu Lys Val
            930                 935                 940

Phe Ser Glu Ala Ala Gln Leu Ile Ala Thr Lys Glu Glu Asn Arg His
945                 950                 955                 960

Leu Phe Leu Pro Gln Cys Leu Tyr Pro Gly Ala Ile Lys Lys Ala Lys
                965                 970                 975

Gly Ala Asp Gln Leu Ser Pro Tyr Tyr Gly Ile Lys Pro Ser Asp Tyr
            980                 985                 990

Ile Ser Gly Ser Leu Val Ile His Asn Thr Asp Ile Glu Gln Ser Arg
        995                 1000                1005

Asn Ala Glu Asn Glu Ser Pro  Lys Gly Gln Ala Ser  Ser Asn Gly
    1010                1015                1020

Cys Ala Ala Leu Lys Lys Asp  Ser Leu Pro Leu Leu  Pro Lys Asn
    1025                1030                1035

Arg Gly Met Val Ile Val Asn  Gly Gly Leu Lys Gln  Asp Glu Arg
    1040                1045                1050

Pro Ala Ala Asn Pro Gln Gln  Glu Asn Ile Ser Gln  Asn Pro Gln
    1055                1060                1065

His Glu Asp Asp His Lys Ser  Pro Ser Trp Ile Ser  Glu Asn Pro
    1070                1075                1080

Leu Ala Ala Asn Glu Asn Val  Ser Pro Gly Ile Pro  Ser Ala Glu
    1085                1090                1095

Glu Gln Leu Ser Ser Ile Ala  Lys Gly Val Asn Gly  Ser Ser Gln
    1100                1105                1110

Ala Pro Thr Ser Gly Lys Tyr  Cys Arg Leu Cys Asp  Ile Gln Phe
    1115                1120                1125

Asn Asn Leu Ser Asn Phe Ile  Thr His Lys Lys Phe  Tyr Cys Ser
    1130                1135                1140

Ser His Ala Ala Glu His Val  Lys
    1145                1150

<210> SEQ ID NO 2
<211> LENGTH: 39
<212> TYPE: DNA
<213> ORGANISM: Artificial Sequence
<220> FEATURE:
<223> OTHER INFORMATION: forward primer for FOG2-ZF-5-m

<400> SEQUENCE: 2
aattatctag tgcgcaaaaa gcgttattgc agcagccga                           39

<210> SEQ ID NO 3
<211> LENGTH: 39
<212> TYPE: DNA
<213> ORGANISM: Artificial Sequence
<220> FEATURE:
<223> OTHER INFORMATION: reverse primer for FOG2-ZF-5-m

<400> SEQUENCE: 3
tcggctgctg caataacgct ttttgcgcac tagataatt                           39

<210> SEQ ID NO 4
<211> LENGTH: 48
<212> TYPE: DNA
<213> ORGANISM: Artificial Sequence
<220> FEATURE:
<223> OTHER INFORMATION: forward primer for FOG2-ZF-6-m

<400> SEQUENCE: 4
gaaacataca tggtccgcaa acagtattac cgtgctacac gccacgac                 48
```

<210> SEQ ID NO 5
<211> LENGTH: 48
<212> TYPE: DNA
<213> ORGANISM: Artificial Sequence
<220> FEATURE:
<223> OTHER INFORMATION: reverse primer for FOG2-ZF-6-m

<400> SEQUENCE: 5
gtcgtggcgt gtagcacggt aatactgttt gcggaccatg tatgtttc         48

<210> SEQ ID NO 6
<211> LENGTH: 27
<212> TYPE: DNA
<213> ORGANISM: Artificial Sequence
<220> FEATURE:
<223> OTHER INFORMATION: forward primer for FOG2[1-412]

<400> SEQUENCE: 6
ggatccatgt cccggcgaaa gcaaagc                                 27

<210> SEQ ID NO 7
<211> LENGTH: 28
<212> TYPE: DNA
<213> ORGANISM: Artificial Sequence
<220> FEATURE:
<223> OTHER INFORMATION: reward primer for FOG2[1-412]

<400> SEQUENCE: 7
gcggccgcgt ggctggctgt aagctgtc                                28

<210> SEQ ID NO 8
<211> LENGTH: 25
<212> TYPE: DNA
<213> ORGANISM: Artificial Sequence
<220> FEATURE:
<223> OTHER INFORMATION: forward primer for FOG[413-789]

<400> SEQUENCE: 8
ggatcccaga cttattgacc agaag                                   25

<210> SEQ ID NO 9
<211> LENGTH: 30
<212> TYPE: DNA
<213> ORGANISM: Artificial Sequence
<220> FEATURE:
<223> OTHER INFORMATION: reverse primer for FOG2[413-789]

<400> SEQUENCE: 9
gcggccgcga tatcacatct tgggtggtag                              30

<210> SEQ ID NO 10
<211> LENGTH: 25
<212> TYPE: DNA
<213> ORGANISM: Artificial Sequence
<220> FEATURE:
<223> OTHER INFORMATION: forward primer for FOG2[802-1151]

<400> SEQUENCE: 10
ggatccctct gacgatcaac aagtg                                   25

<210> SEQ ID NO 11
<211> LENGTH: 25
<212> TYPE: DNA
<213> ORGANISM: Artificial Sequence
<220> FEATURE:
<223> OTHER INFORMATION: reverse primer for FOG2[802-1151]

<400> SEQUENCE: 11 ggatcccctct gacgatcaac aagtg          25

<210> SEQ ID NO 12
<211> LENGTH: 27
<212> TYPE: DNA
<213> ORGANISM: Artificial Sequence
<220> FEATURE:
<223> OTHER INFORMATION: forward primer for FOG2[1-506]

<400> SEQUENCE: 12
ggatccatgt cccggcgaaa gcaaagc          27

<210> SEQ ID NO 13
<211> LENGTH: 32
<212> TYPE: DNA
<213> ORGANISM: Artificial Sequence
<220> FEATURE:
<223> OTHER INFORMATION: reverse primer for FOG2[1-506]

<400> SEQUENCE: 13
gcggccgctc atttgacatg ttctgctgca tg          32

<210> SEQ ID NO 14
<211> LENGTH: 27
<212> TYPE: DNA
<213> ORGANISM: Artificial Sequence
<220> FEATURE:
<223> OTHER INFORMATION: forward primer for FOG2[1-789]

<400> SEQUENCE: 14
ggatccatgt cccggcgaaa gcaaagc          27

<210> SEQ ID NO 15
<211> LENGTH: 31
<212> TYPE: DNA
<213> ORGANISM: Artificial Sequence
<220> FEATURE:
<223> OTHER INFORMATION: reverse primer for FOG2[1-789]

<400> SEQUENCE: 15
gcggccgctc atttgacatg ttctgctgca t          31

<210> SEQ ID NO 16
<211> LENGTH: 16
<212> TYPE: PRT
<213> ORGANISM: Artificial Sequence
<220> FEATURE:
<223> OTHER INFORMATION: ZF-3-wt-21 peptide, FOG2[335-355]

<400> SEQUENCE: 16

Leu Lys Cys Thr Val Cys Ser Tyr Thr Ala Asp Ser Val Ile Asn Phe
1               5                   10                  15

<210> SEQ ID NO 17
<211> LENGTH: 24
<212> TYPE: PRT
<213> ORGANISM: Artificial Sequence
<220> FEATURE:
<223> OTHER INFORMATION: ZF-5-wt-24 peptide, FOG2[548-571]

<400> SEQUENCE: 17

Ala Thr Cys Phe Glu Cys Asn Ile Thr Phe Asn Asn Leu Asp Asn Tyr
1               5                   10                  15

Leu Val His Lys Lys His Tyr Cys

```
<210> SEQ ID NO 18
<211> LENGTH: 24
<212> TYPE: PRT
<213> ORGANISM: Artificial Sequence
<220> FEATURE:
<223> OTHER INFORMATION: ZF-5-m-24 peptide, FOG2[548-571]

<400> SEQUENCE: 18

Ala Thr Cys Phe Glu Cys Asn Ile Thr Phe Asn Asn Leu Asp Asn Tyr
1               5                   10                  15

Leu Val Ala Lys Lys Ala Tyr Cys
            20

<210> SEQ ID NO 19
<211> LENGTH: 20
<212> TYPE: PRT
<213> ORGANISM: Artificial Sequence
<220> FEATURE:
<223> OTHER INFORMATION: ZF-5-wt-20 peptide, FOG2[550-569]

<400> SEQUENCE: 19

Cys Phe Glu Cys Asn Ile Thr Phe Asn Asn Leu Asp Asn Tyr Leu Val
1               5                   10                  15

His Lys Lys His
            20
```